United States Patent

Redha

Patent Number: 5,902,313
Date of Patent: May 11, 1999

[54] MEDICAL INSTRUMENT FOR ATHERECTOMY

[76] Inventor: Falah Redha, Am Pfisterhölzli 15, 8606 Greifensee, Switzerland

[21] Appl. No.: 08/999,485

[22] Filed: Dec. 29, 1997

Related U.S. Application Data

[63] Continuation-in-part of application No. 08/335,870, filed as application No. PCT/EP94/00730, Mar. 9, 1994, Pat. No. 5,725,543.

[51] Int. Cl.$^6$ .................................................. A61B 17/22
[52] U.S. Cl. ............................................................ 606/159
[58] Field of Search .................................... 606/159, 170, 606/160, 167, 180, 114

[56] References Cited

U.S. PATENT DOCUMENTS

| | | |
|---|---|---|
| 2,868,206 | 1/1959 | Stoesser . |
| 3,230,949 | 1/1966 | Rodriguez-Olleros . |
| 3,508,553 | 4/1970 | Kanbar et al. . |
| 3,764,427 | 10/1973 | Reimels . |
| 3,837,345 | 9/1974 | Matar . |
| 4,273,128 | 6/1981 | Lary . |
| 4,493,321 | 1/1985 | Leather . |
| 4,685,458 | 8/1987 | Leckrone . |
| 4,747,821 | 5/1988 | Kensey et al. . |
| 4,765,332 | 8/1988 | Fischell et al. . |
| 4,794,928 | 1/1989 | Kletschka . |
| 4,842,579 | 6/1989 | Shiber . |
| 4,886,061 | 12/1989 | Fischell et al. . |
| 4,952,215 | 8/1990 | Ouriel et al. . |
| 4,957,482 | 9/1990 | Shiber . |
| 5,026,383 | 6/1991 | Nobles . |
| 5,047,041 | 9/1991 | Samuels . |
| 5,049,154 | 9/1991 | Quadri . |
| 5,053,044 | 10/1991 | Mueller et al. . |
| 5,061,240 | 10/1991 | Cherian . |
| 5,069,679 | 12/1991 | Taheri . |
| 5,071,424 | 12/1991 | Reger . |
| 5,074,871 | 12/1991 | Groshong . |
| 5,085,659 | 2/1992 | Rydell . |
| 5,100,426 | 3/1992 | Nixon . |
| 5,133,725 | 7/1992 | Quadri . |
| 5,152,772 | 10/1992 | Sewell, Jr. . |
| 5,152,773 | 10/1992 | Redha . |
| 5,154,724 | 10/1992 | Andrews . |
| 5,282,813 | 2/1994 | Redha . |
| 5,522,825 | 6/1996 | Kropf et al. . |
| 5,556,408 | 9/1996 | Farhat ...................................... 606/159 |
| 5,601,580 | 2/1997 | Goldberg et al. ........................ 606/159 |
| 5,658,302 | 8/1997 | Wicherski et al. ...................... 606/159 |

FOREIGN PATENT DOCUMENTS

| | | |
|---|---|---|
| 0117519 | 2/1984 | European Pat. Off. . |
| 1585065 | 1/1970 | France . |
| 1909080 | 6/1964 | Germany . |
| 7908610 | 6/1979 | Germany . |
| 3320984 | 2/1984 | Germany . |
| 3800777 | 7/1988 | Germany . |
| 2044103 | 3/1979 | United Kingdom . |
| 8800458 | 1/1988 | WIPO . |
| 8907914 | 9/1989 | WIPO . |
| 8909029 | 10/1989 | WIPO . |

Primary Examiner—Michael Buiz
Assistant Examiner—Kevin Truong
Attorney, Agent, or Firm—Pauley Petersen Kinne & Fejer

[57] ABSTRACT

A medical instrument for removing deposits on the walls of arteries and/or veins having at least one partially hollow body that can be introduced into the arteries and/or veins and a plurality of cutting bodies with cutting edges for removal of the deposits. A base body protrudes at least partially into the partially hollow body and the cutting bodies and fixedly connected to the base body.

29 Claims, 11 Drawing Sheets

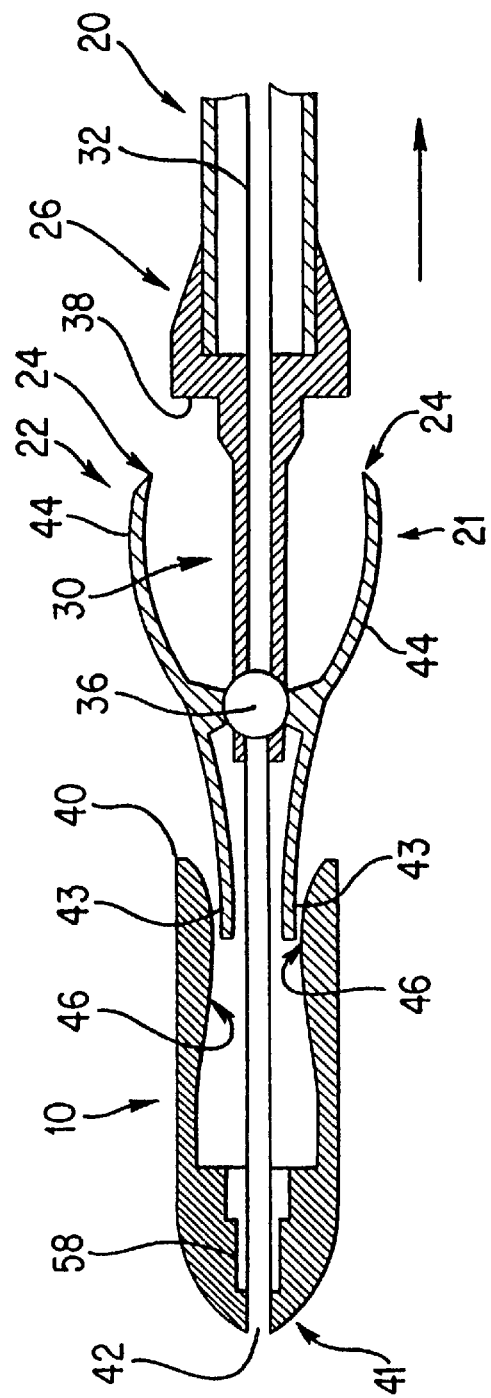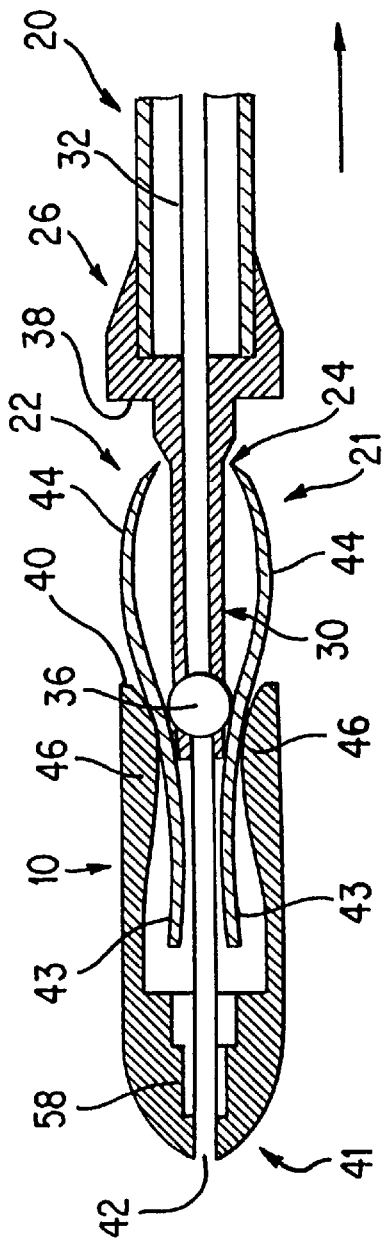
FIG. 1
FIG. 2

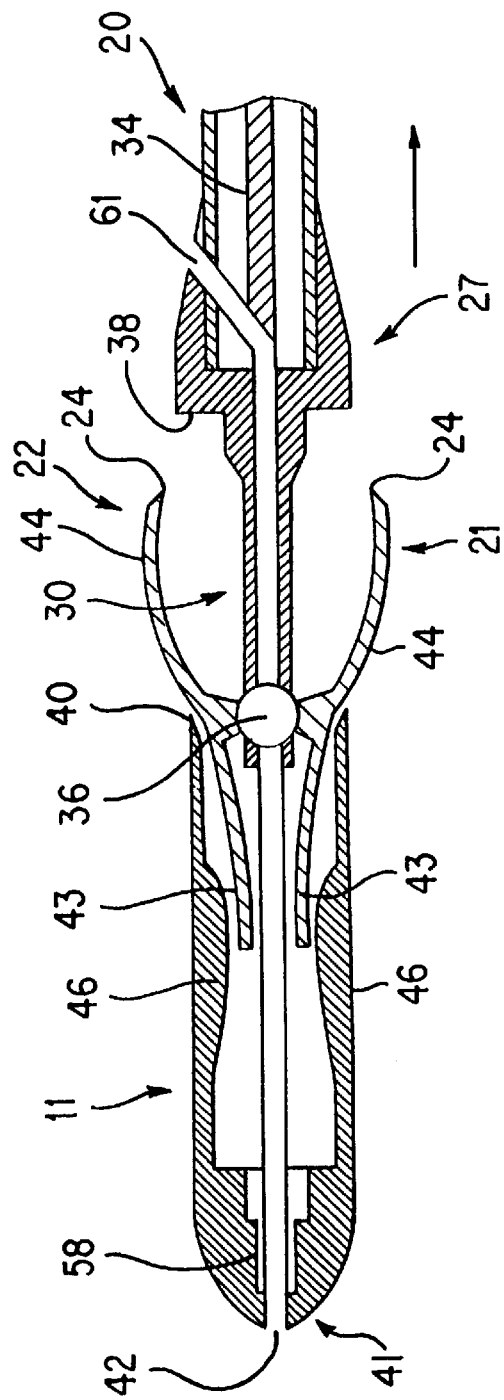
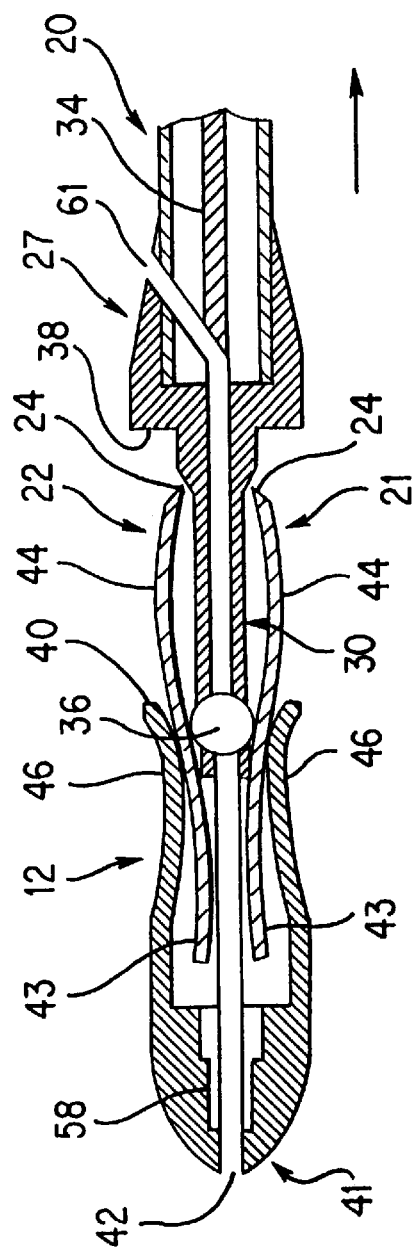
FIG. 6
FIG. 7

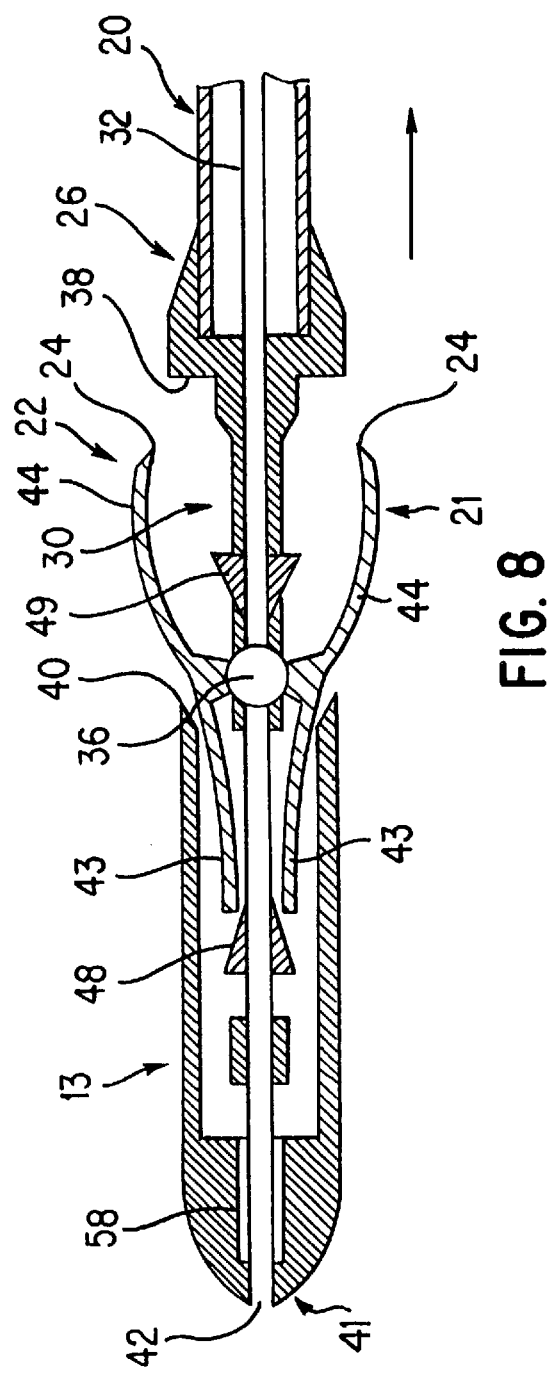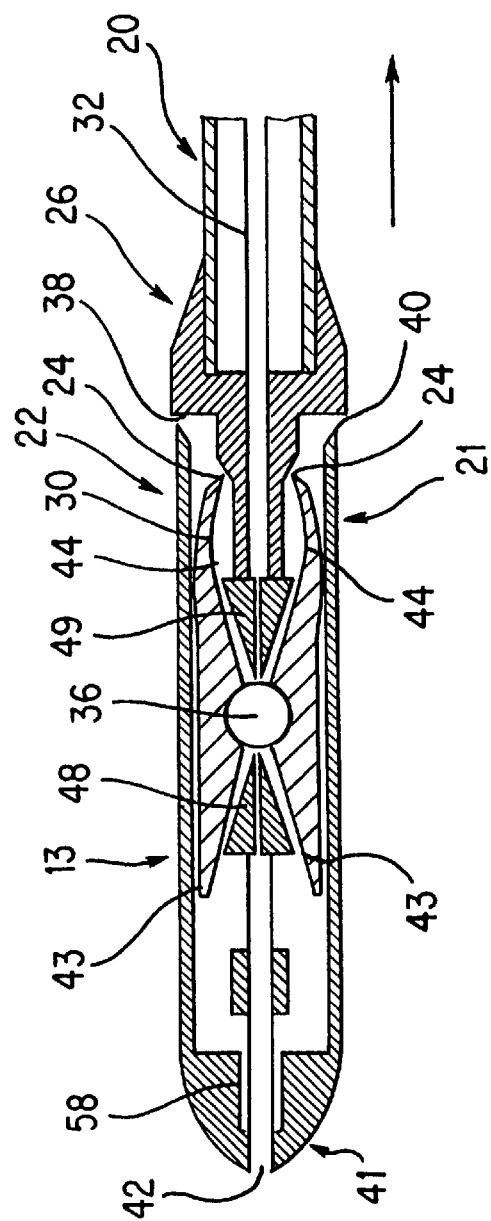
FIG. 8
FIG. 9

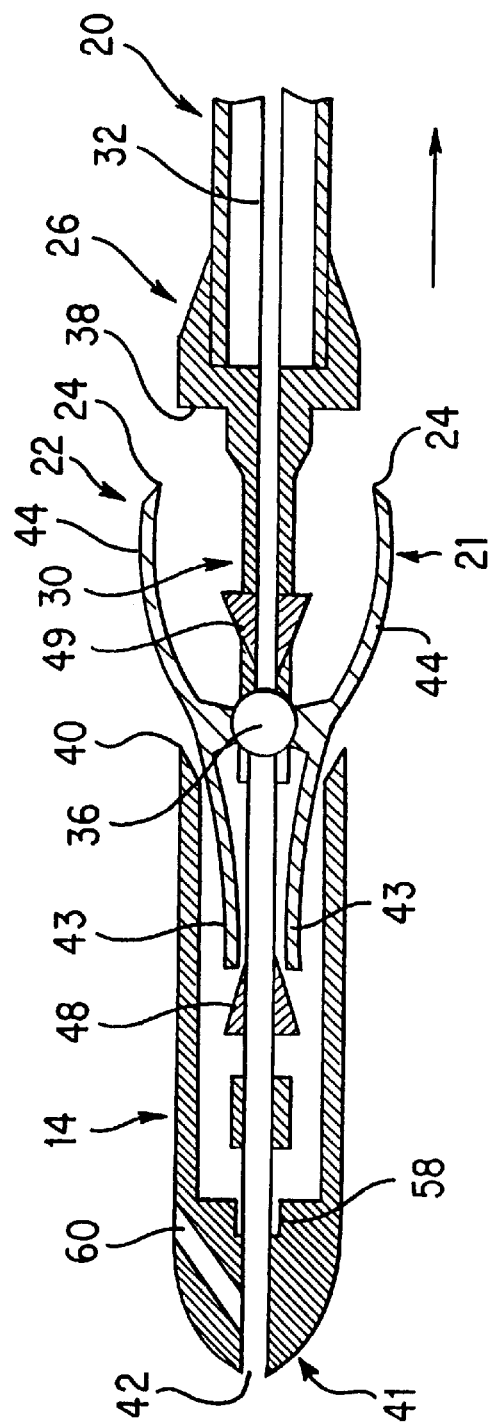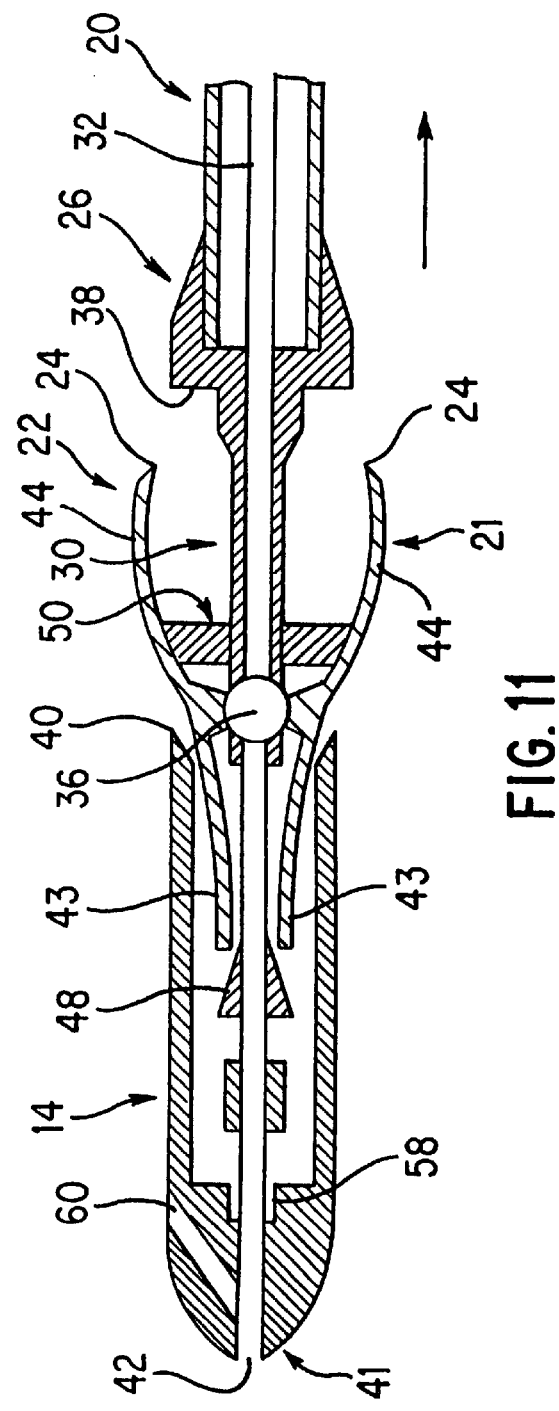

MEDICAL INSTRUMENT FOR ATHERECTOMY

CROSS-REFERENCE TO RELATED APPLICATION

This application is a continuation-in-part application of U.S. patent application Ser. No. 08/335,870 filed May 23, 1995, now U.S. Pat. No. 5,725,543, which is a 371 of PCT/EP94/00730, filed Mar. 9, 1994.

BACKGROUND OF THE INVENTION

1. Field of the Invention

This invention relates to a medical instrument for removing deposits from the walls of hollow organs within the body, such as arteries, veins, bile ducts, urethra and the like, having a partially hollow body suitable for insertion into such vessels, a traction and/or actuation means that can be removed from the vessels, and cutting bodies with cutting edges disposed toward the traction direction, which cutting bodies remove the deposits.

2. Description of Prior Art

In known instruments of this type, as taught, for example, by U.S. Pat. No. 4,765,332, an approximately cylindrical base body is provided that has cutting portions that are likewise cylindrical and that point in the traction direction. The sharp edges of the cutting portions taper from the inside outward, which can cause injury even to healthy vessels. In addition, adaptation to the walls of arteries or veins is possible only to a limited extent.

SUMMARY OF THE INVENTION

It is an object of this invention is to provide a medical instrument of the type discussed hereinabove whereby the effective cross section of the instrument can be enlarged simply and adapted to the vessels.

This and other objects are attained by a medical instrument in accordance with one embodiment of this invention having elements of known medical instruments as set forth hereinabove and further comprising a base body protruding at least partially into the hollow body and cutting bodies extending in the traction direction connected to said base body.

This instrument can be introduced by a catheter into the vessel up to the intended point, which can be located using a contrast medium. The catheter and the body are disposed in such a way that the plaque is between the body and the catheter. The traction means is then actuated at the intended point and the cutting bodies are exposed, whereupon the instrument is retracted, thereby partially burying the cutting bodies between the plaque and the vessel walls. The traction means is then activated again, thus cutting off the plaque. This process is repeated until the inside wall is smooth. The chips produced in this planing process can either be removed by suction or entrained by the body, which body is removed from the artery after the operation.

In accordance with one embodiment of this invention, the portion of the base body protruding into the body is a tubular member, in which is disposed a device for adjusting the body relative to the cutting bodies.

This device, in accordance with one embodiment of this invention, comprises a length of tube or wire that is actuatable from outside the vessel. Actuation of the device exerts pressure on the cutting bodies, thereby enlarging or shrinking the effective cross section of the cutting body, depending specifically on direction of movement of the body.

In accordance with another embodiment of this invention, the cutting bodies comprise a pivot shaft which extends transversely to the traction direction of the body. This assures that the cutting edges point toward the user, and that the cutting bodies can assume their effective or ineffective position. In the context of this embodiment of the invention, the cutting bodies are embodied as one-or two-armed levers, which, in their rest position, are accommodated entirely or virtually entirely inside the body. The base body comprises a stop member, which, in the rest position of the cutting bodies, is disposed virtually unspaced apart from one end face of the body. The advantage of this embodiment is that introducing the instrument into vessels is facilitated markedly because the cutting edges do not come into contact with the vessel.

In accordance with one embodiment of this invention, the body is essentially embodied as a hollow cylinder which receives the cutting bodies in their rest position.

In accordance with yet another embodiment of this invention the face end, remote from the user, of the body has an opening extending in the traction direction. The opening may serve to receive a guide means, for instance a thin length of wire, by which introducing the instrument to the intended point can be facilitated. Preferably, the face end of the body remote from the user is convex and free of edges.

In accordance with yet another embodiment of this invention, attached to the remote face of the partially hollow body is a stiff or flexible tube or reinforced tube, or a spiral or spirals that facilitates maneuvering of the device in the hollow structures of its intended use.

In accordance with a further embodiment of this invention, two cutting bodies, having a common pivot shaft and each having one force arm and one load arm are provided. The inner wall of the body comprises pressure bodies which, in their operating position, are pressure-connected to the respective force arm and, in their rest position, are pressure-connected to the respective load arm of the cutting bodies. The pressure bodies may be embodied as radial protrusions with slide curves. The advantage of this embodiment is that the cutting bodies are either opened or closed by axially shifting the body in the traction direction. When they open, the cutting bodies protrude from the body, and pressure is exerted by the body on the respective force arm of the cutting body, so that the cutting bodies open and are located outside the body. The cutting edges or cutting bodies define a circle or an ellipse, which is located outside the body. To enable continuous actuation of the cutting bodies, the external profile of the longitudinal section of the respective cutting body is curved. This assures a gradual opening and closing of the cutting bodies as applicable.

In accordance with yet another embodiment of this invention, the device, embodied as a length of cable, tube or wire, comprises clamping bodies, which, depending on the operating position of the cutting bodies, cooperate with the force arm or the load arm of the respective cutting body. The clamping bodies are embodied as wedge-shaped in axial cross section and face one another with their tapered face ends. In accordance with one preferred embodiment, two clamping bodies are provided, between which the pivot shaft of the cutting bodies is disposed. One of the clamping bodies is carried by the base body and comprises an elastically deformable material. In that case, only one of the clamping bodies executes relative motions with respect to the pivot shaft of the cutting bodies.

In accordance with yet another embodiment the flanks, adjoining the cutting edges, of the cutting bodies are at least in part provided with cutting portions. As a result, when the cutting bodies close, not only the face-end cutting edges, but also the edges extending longitudinally of the cutting bodies, act as cutting devices.

In accordance with one particularly preferred embodiment of this invention, the cutting bodies comprise formed-on leaflet springs and/or shape memory alloy metal. This embodiment of the invention exploits the fact that certain metals, after undergoing deformation, resume their original shape. It is therefore possible to embody the cutting bodies such that, in their original position, they assume the desired operating position. Before the instrument is used, the cutting bodies are deformed (retracted position) and held at a certain temperature. Inside the veins, the operating temperature of the instrument changes; the cutting bodies expand and assume their operating position. This makes a complicated mechanism for pivotably connecting, displacing and adjusting the cutting bodies unnecessary.

In accordance with yet another embodiment of this invention, the base body, protrudes at least partway into the body and the cutting bodies, extending in the traction direction, are secured, for instance by screws, welding, hard soldering, cold deformation or the like, to the base body and their operating and rest position is definable by adjustment of the body in the traction direction. In accordance with one embodiment, the cutting bodies comprise an elastically deformable material, such as metal, ceramic, plastic, or alloys. In accordance with this embodiment of the invention, the body, the base body, and parts of the cutting body are made of electrically conductive material and are coated with an insulator, such as Teflon®.

Finally, in accordance with a particularly preferred embodiment of the invention a plurality of pairs of cutting bodies are disposed in series, so that as a result, the deposits can be eliminated faster.

BRIEF DESCRIPTION OF THE DRAWINGS

These and other objects and features will be better understood from the following detailed description taken in conjunction with the drawings wherein:

FIG. 1 is a longitudinal cross-sectional view of the medical instrument in an operating position in accordance with one embodiment of this invention;

FIG. 2 is a longitudinal cross-sectional view of the medical instrument shown in FIG. 1, in a rest position;

FIG. 6 is a longitudinal cross-sectional view of the medical instrument in an operating position in accordance with another embodiment of this invention;

FIG. 7 is a longitudinal cross-sectional view of the instrument in a closed position in accordance with one embodiment of this invention;

FIG. 8 is a longitudinal cross-sectional view of the medical instrument with pressure bodies in an operating position in accordance with one embodiment of this invention;

FIG. 9 is a longitudinal cross-sectional view of the medical instrument shown in FIG. 8 in a rest position;

FIG. 10 is a longitudinal cross-sectional view of the medical instrument with clamping bodies and a transverse bore in an operating position in accordance with one embodiment of this invention;

FIG. 11 is a longitudinal cross-sectional view of the medical instrument with elastic clamping bodies in an operating position in accordance with one embodiment of this invention;

DESCRIPTION OF PREFERRED EMBODIMENTS

Figure 3:
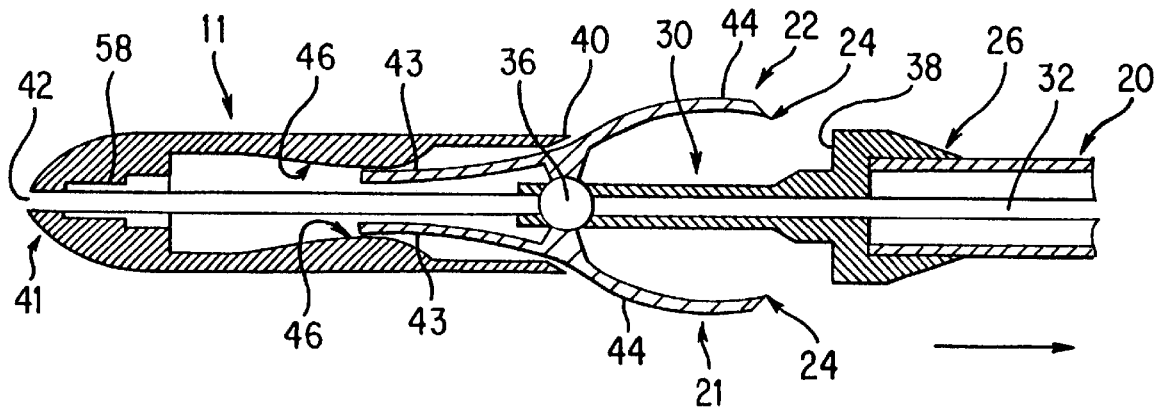
FIG. 3 is a longitudinal cross-sectional view of the medical instrument in an operating position in accordance with another embodiment of this invention.

In the drawings, medical instruments for eliminating deposits in the walls of arteries and/or of veins in accordance with this invention are shown, each comprising one at least partially hollow body 10–14 that can be introduced into the vessels, with a traction and/or actuation means 20 that can be extended out of the vessels, and with cutting bodies 21, 22, pointing in the traction direction and eliminating the deposits, the cutting bodies having cutting edges 24. A base body 26, 27 protruding at least partway into the at least partially hollow body 10–14 is provided, to which the cutting bodies 21, 22 extending in the traction direction are pivotally connected. The operating or rest position of the base body is definable by adjusting the at least partially hollow body 10–14 in the traction direction. The portion 30 of the base body 26, 27 protruding into the respective at least partially hollow body 10–14 is embodied as a tubular portion, in which a device 32, 34 is disposed for relative adjustment of the at least partially hollow body 10–14 with respect to the cutting bodies 21, 22. The device 32, 34 is embodied as a length of tube or wire that is actuatable from outside. The pivot shaft 36 of the cutting bodies 21, 22 extends transversely to the traction direction of the at least partially hollow body 10–14.

The cutting bodies 21, 22 are embodied as two-armed levers, which, in their rest position, are accommodated completely or virtually completely inside the at least partially hollow body 10–14. The base body 26 or 27 has a stop portion 38, which, in the rest position of the cutting bodies 21, 22, is disposed virtually unspaced apart from one end face 40 of the at least partially hollow body 10–14. The respective at least partially hollow body 10–14 is essentially embodied as a hollow cylinder, which receives the cutting bodies 21, 22 in their rest position. The face end 41, remote from the user, of the at least partially hollow body 10–14 forms an opening 42 extending in the traction direction, into which the end piece of the device 32 or 34 protrudes and is secured. The face end 41 of the at least partially hollow body 10–14 remote from the user is convex and free of edges.

The drawings also show a medical instrument in accordance with this invention comprising two cutting bodies 21, 22 having a common pivot shaft 36 and each cutting body 21, 22 having one force arm and one load arm 43, 44. The inner wall of the at least partially hollow body 10, 11, 12 comprises pressure bodies 46, which in their operating position are pressure-connected to the respective force arm 43 and in their rest position are pressure-connected to the respective load arm 44 of the cutting bodies 21 and 22. The pressure bodies 46 are embodied as radial protrusions with slide curves that extend in the axial direction. The external outline of the longitudinal section of the respective cutting body is curved so that a continuous opening or closing of the cutting bodies is assured.

The device 32, 34, embodied as a length of cable, tube or wire, comprises clamping bodies 48, 49 and 50 (see FIGS. 8–11), which, depending on the operating position of the cutting bodies 21, 22, cooperate with the force or load arm 43, 44 of the respective cutting body 21, 22. The clamping bodies 48, 49 and 50 have a wedge-shaped axial cross section and face one another with their tapered face ends. Two clamping bodies 48, 49 and 50 each are provided, between which the pivot shaft 36 of the cutting bodies 21, 22 is disposed. The clamping body 50 shown in FIG. 11 is connected to the base body 26 and comprises an elastically deformable material.

In accordance with the embodiment of the medical instrument of this invention shown in FIGS. 1 and 2, the at least partially hollow body 10 does not receive the cutting bodies 21 and 22 in their entirety, in their rest position (FIG. 2). However, the cutting edges 21 are disposed upstream of the stop 38, so that no cutting can occur. Cutting is assured only once the at least partially hollow body 10 is spaced apart by an approximately maximal distance from the pivot shaft 36 and its pressure bodies 46 exert pressure upon the force arms 43, so that the cutting edges 24 are disposed maximally far apart from one another and protrude past the base body 26. That is, the outer circumference of the base body 26 is not smaller than the outer circumference of the two cutting edges 24. Because the cutting bodies 21 and 22 are pivotably connected to the portion 30, which is embodied as a length of tube, the at least partially hollow body 10 moves away from pivot shaft 36 when the device 32, which is likewise embodied as a length of tube, is displaced, whereby force is exerted on the force arms 43. A guide body, such as a length of wire, can be introduced into the device 32; this guide body protrudes out of the opening 42 and can serve to introduce the instrument into the vessels. If the device 32 is actuated in the direction of the arrow, then the spacing between the at least partially hollow body 10 and the pivot shaft 36 is reduced, and the pressure bodies 46 exert pressure on the load arms 44, causing the instrument to assume the position shown in FIG. 2.

Figure 4:
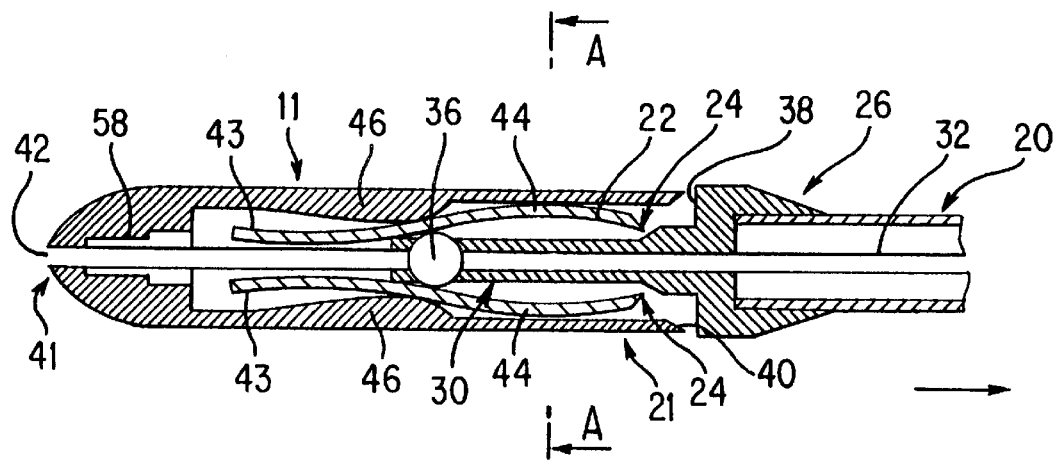
FIG. 4 is a longitudinal cross-sectional view of the medical instrument shown in FIG. 3 in a rest position.
Figure 5:
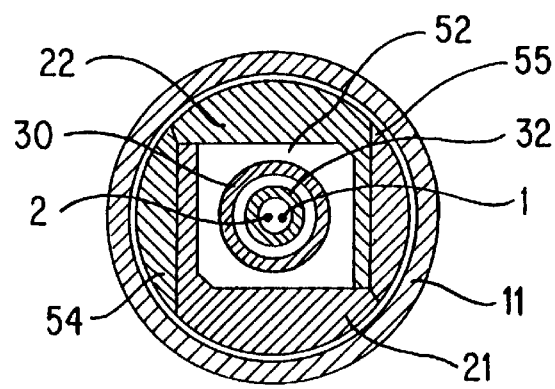
FIG. 5 is a transverse cross-sectional view taken along the line A—A in FIG. 4.

FIGS. 3–5 show another embodiment of the instrument of this invention, which differs from the instrument shown in FIGS. 1 and 2 in that the body 11 is dimensioned such that, in the closed or rest position of the instrument, both cutting bodies 21 and 22 are disposed in their entirety within body 11 (see FIG. 4). The periphery of the cross section of the body 11 is circular. The base body 26 has the same periphery as the body 11, so that the body 11 is flush with the base body 26 in the closed position. As a result, insertion of the instrument into the vessels is especially simple.

In accordance with the embodiment shown in FIG. 5, the flanks 54 and 55 extending in the traction direction of the instrument are also embodied as cutting bodies, so that not only the face end but the long sides as well can be used for cutting. The device 32 is dimensioned such that it can simultaneously serve to guide an angioscope 3 and a guide body 1 as well.

In accordance with the embodiment of this invention shown in FIG. 7, the body 12 has a diameter reduction in its middle region. As a result, a protrusion is formed for actuating the force or load arm of the respective cutting body. The base body 27 forms a lateral transverse bore 61, into which a guide body whose free end can protrude from the opening 42 can be introduced. In this case, the device 34 is embodied as a length of wire.

The embodiment of this invention shown in FIG. 6 is also provided with a transverse bore 61, and the body 11 is dimensioned such that it can entirely receive the cutting bodies, as in the embodiment shown in FIG. 3.

In accordance with the embodiment shown in FIGS. 8–11, the device 32 or 34, embodied as a length of cable, tube or wire, carries clamping bodies 48, 49 and 50, which, depending on the operating position of the cutting bodies 21 and 22, cooperate with the force arm 43 and load arm 44 of the respective cutting body 21 and 22. By relative adjustment of the device 42 with respect to the base body 26, the clamping bodies 48 and 49 are likewise adjusted with respect to the pivot shaft 36, and they exert pressure on the inside of the respective load or force arm, causing that arm to be swiveled inward or outward, as applicable. In the embodiment of the instrument shown in FIG. 10, the device 32 is a length of wire. To enable problem-free introduction of the body 14 into the vessel in this case as well, a transverse bore 60, into which a length of guide wire can be introduced, is embodied in the face-end portion of the body 14.

In accordance with the embodiment of this invention shown in FIG. 11, the clamping bodies 50 are permanently connected to the portion 30 and comprise an elastically deformable material. It is therefore necessary only to shift the clamping body 48. If the clamping body 48 does not engage the force arms 43, then the clamping bodies 50 exert force on the load arms 44, swiveling them outward and causing them to assume the position shown in FIG. 11.

Figure 12:
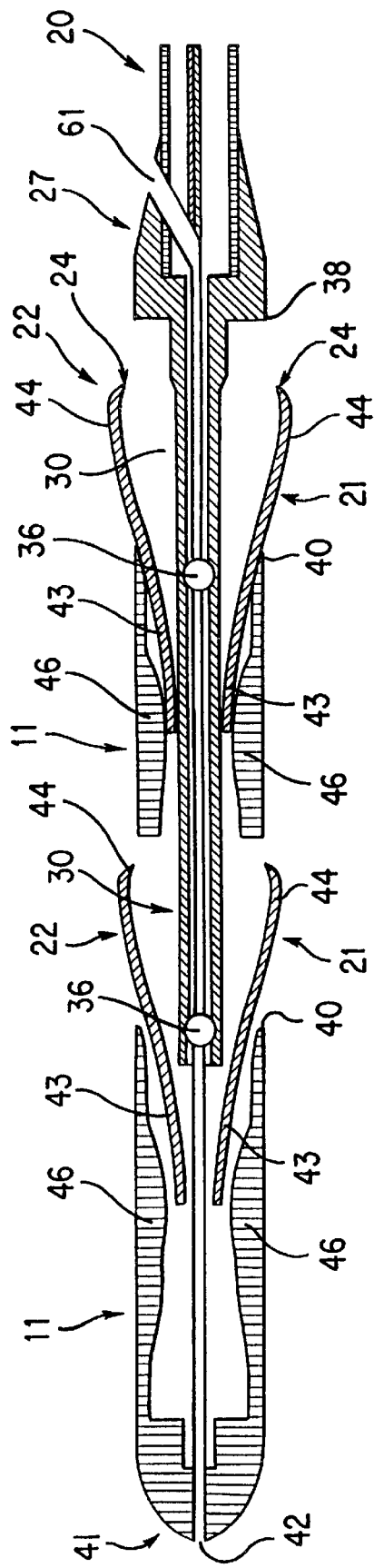
FIG. 12 is a longitudinal cross-sectional view of the medical instrument in a tandem version in accordance with one embodiment of this invention.

In the embodiment of this invention shown in FIG. 12, two pairs of cutting bodies 21, 22 are disposed in series and are adjustable by the same actuating means 20. Very generally, three, four or more pairs of cutting bodies could also be used. The cutting bodies 21, 22 comprise formed-on leaflet springs and/or shape memory alloy metal.

Figure 13:
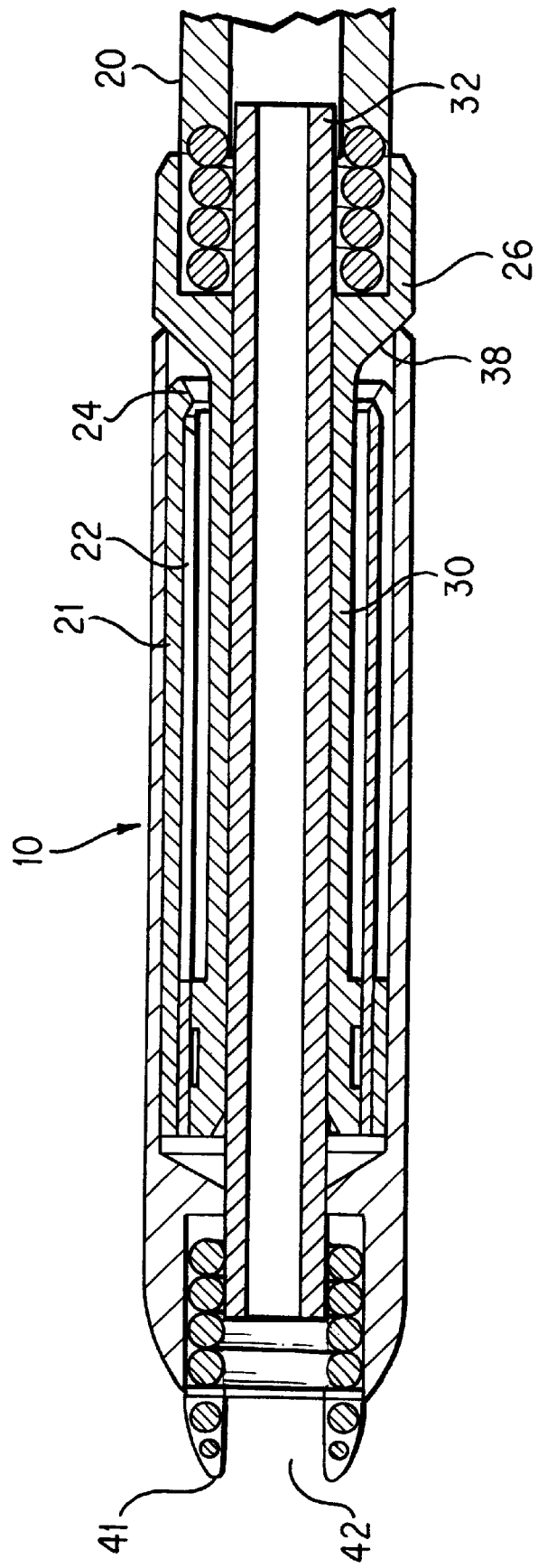
FIG. 13 is a longitudinal cross-sectional view of the medical instrument of this invention having cutting bodies constructed of leaflet springs, shape memory alloys and the like and having a short, flexible, optionally conical, guiding tube/spiral attached to the tip.
Figure 14:
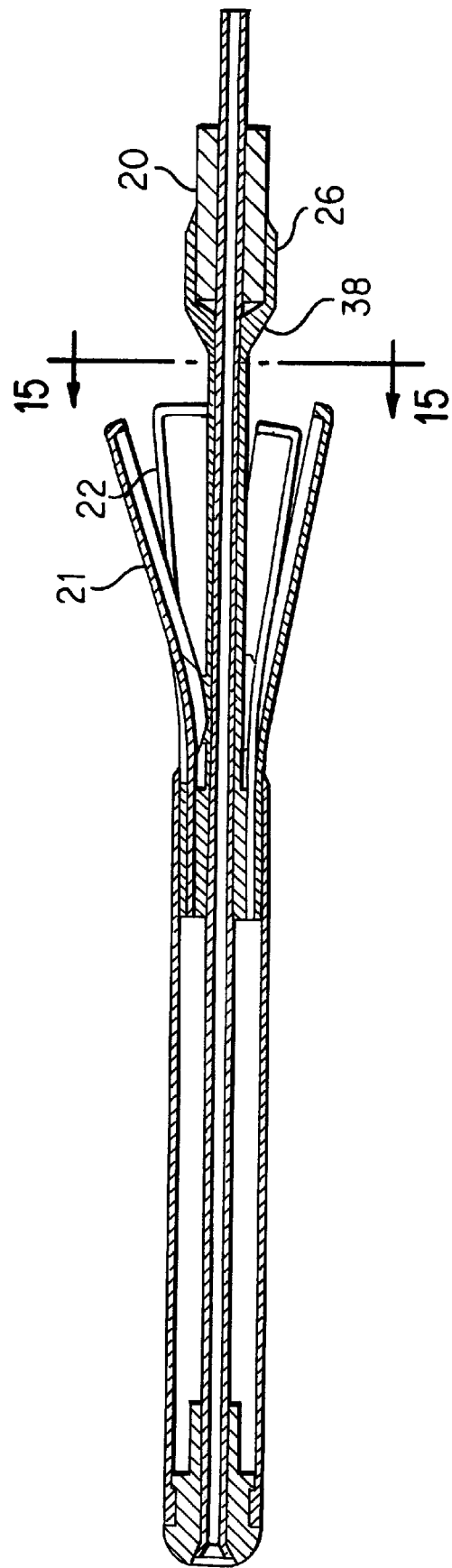
FIG. 14 is a longitudinal cross-sectional view of the medical instrument shown in FIG. 13 with the cutting bodies in an extended mode.
Figure 15:
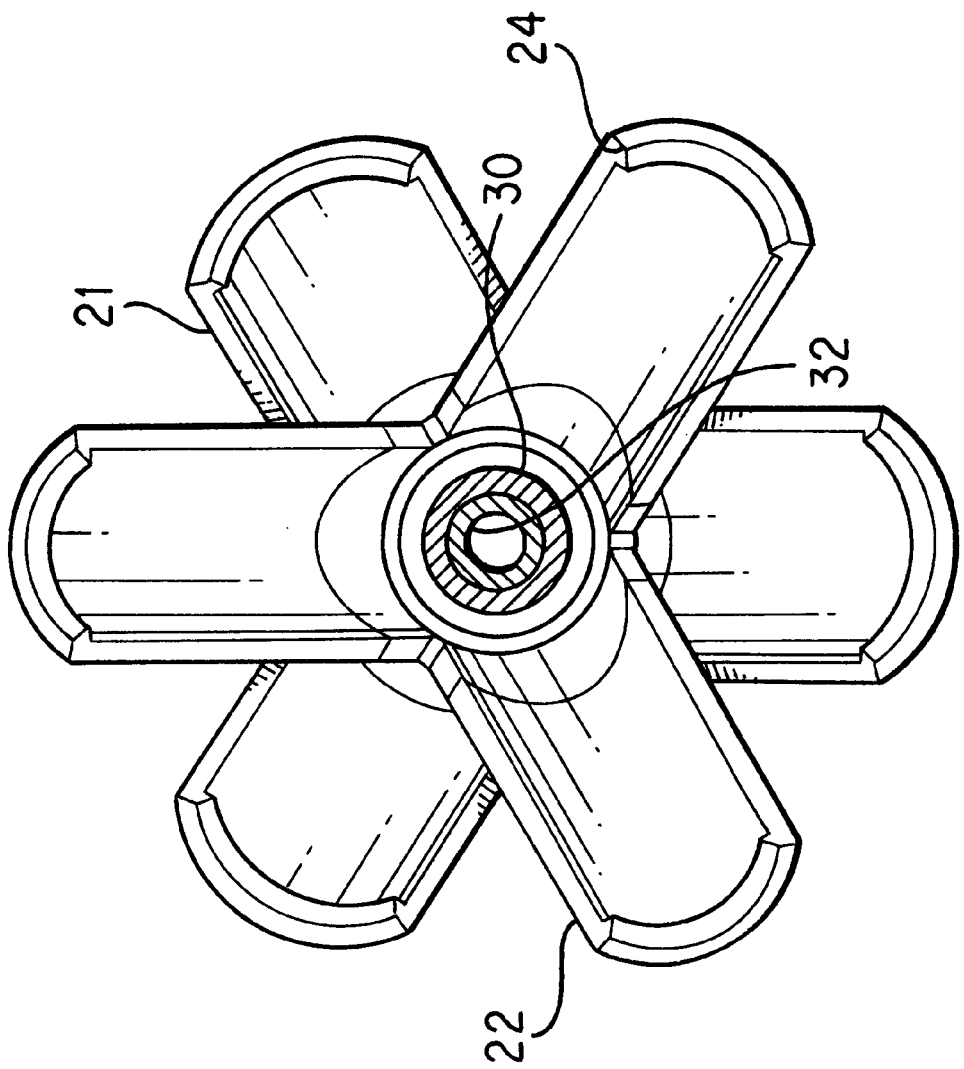
FIG. 15 is a lateral cross-sectional view of the medical instrument of this invention along the line B—B shown in FIG. 14.
Figure 16:
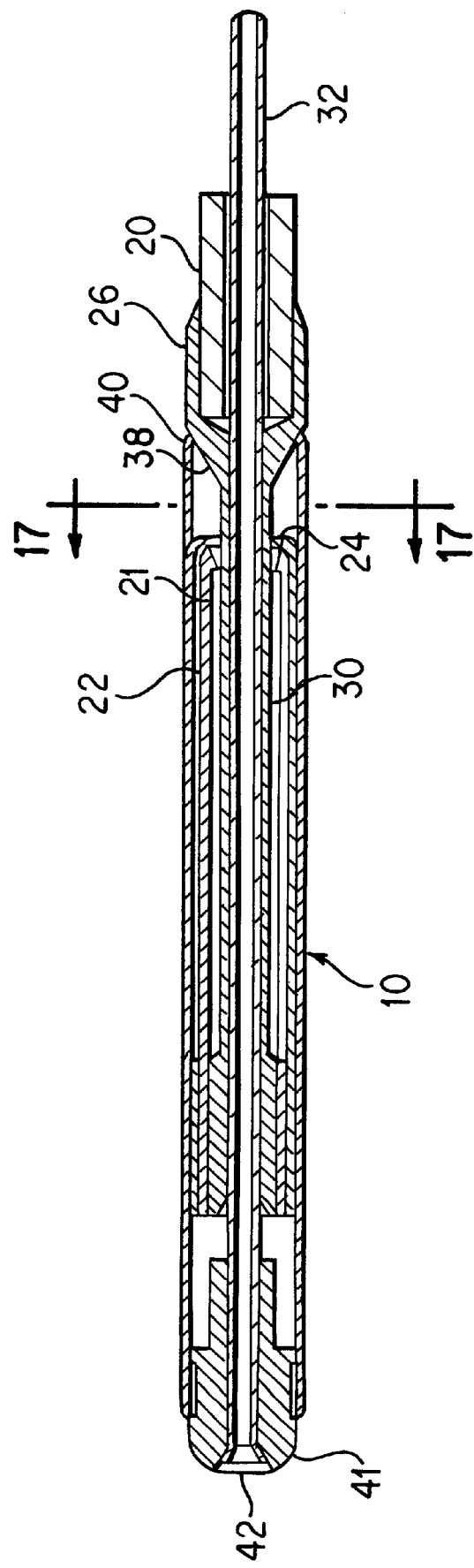
FIG. 16 is a longitudinal cross-sectional view of one embodiment of the medical instrument of this invention having cutting bodies constructed of leaflet springs, shape memory alloys and the like and having a short, flexible, optionally conical guiding tube/spiral attached to the tip.
Figure 17:
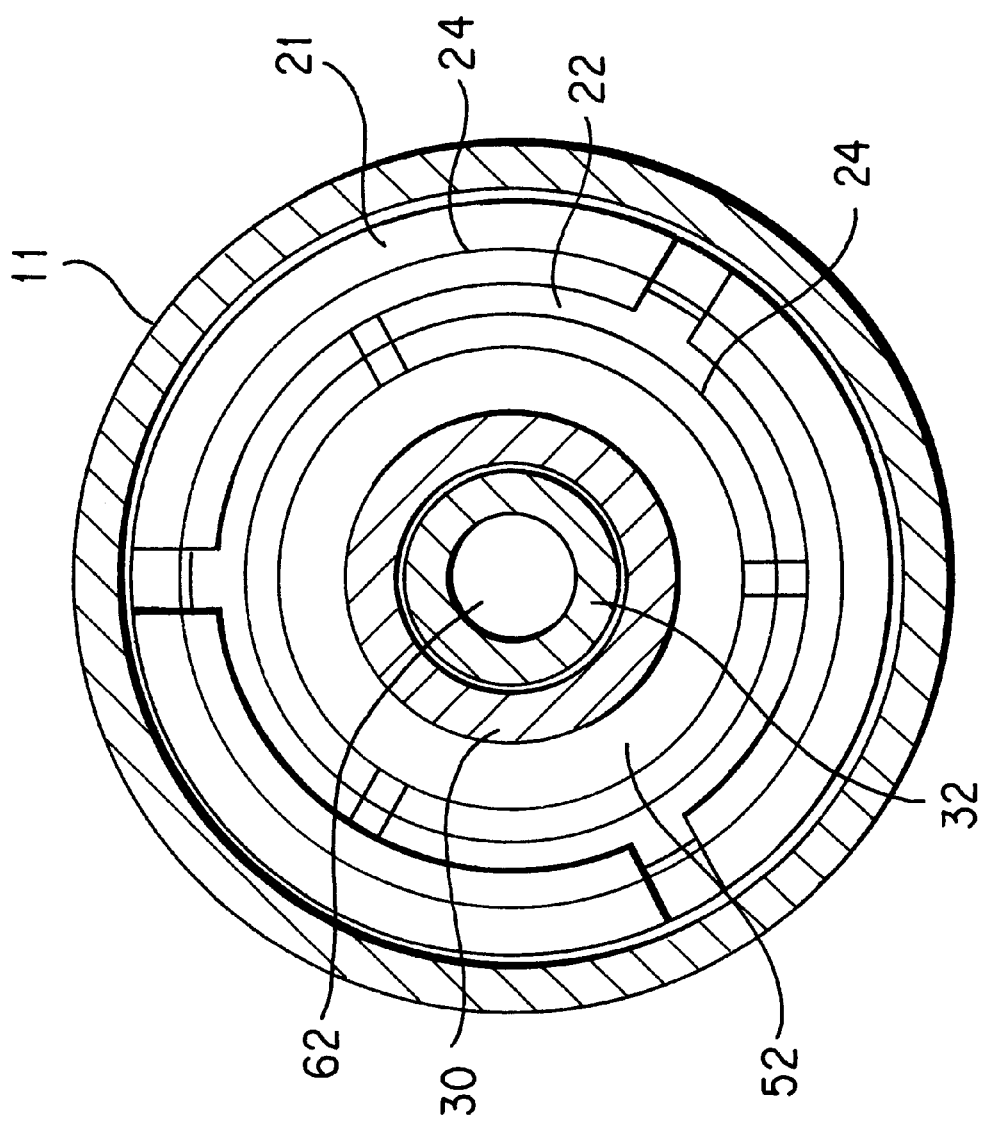
FIG. 17 is a lateral cross-sectional view of the medical instrument of this invention along the line C—C shown in FIG. 16.

FIGS. 13–17 show one embodiment of this invention in which the cutting bodies 21, 22 comprise formed-on leaflet springs and/or shape memory material, such as shape memory alloy metal. In accordance with this embodiment, cutting bodies 21, 22 are made from cylinders of any material having suitable elasticity and hardness including, but not limited to, metal, metal alloy, shape memory alloy, superelastic metal alloy, plastic, or shape memory plastic. The cylinders are partially cut in a longitudinal direction so as to form the cutting bodies 21, 22. The cutting bodies 21, 22 thus formed are bent outward and subsequently heat treated in such a way that the material sustains a permanent shape and possesses elastic properties. In accordance with one embodiment, two such cutting body assemblies are concentrically disposed so as to provide cutting bodies 21, 22 which partially overlap. The cutting bodies 21, 22 are then fixedly connected to base body 26, 27. Base body 26, 27 forms longitudinal bore 62. Partially hollow body 10, when slid over cutting bodies 21, 22 acts to compress cutting bodies 21, 22 towards the longitudinal axis of base body 26, 27 and resulting in circumferential disposition of partially hollow body 10 around cutting bodies 21, 22 as shown in FIG. 13. Upon retraction of partially hollow body 10 from around cutting bodies 21,22, cutting bodies 21, 22 are released and resume their outwardly disposed shape, as shown in FIG. 14.

Alternatively, cutting bodies 21, 22 may be made individually and then connected to base body 26, 27, or to each other, or both. In accordance with one embodiment, cutting bodies 21, 22 are fixedly connected to base body 26, 27 by at least one of screws, molding, soldering, glue, hard soldering, hot or cold deformation, or any other suitable method.

Materials suitable for use in constructing the device are preferably selected from the group consisting of metal, metal alloy, shape memory alloy, superelastic metal alloy, plastic, shape memory plastic and combinations thereof.

In accordance with one embodiment of this invention, surfaces or portions of surfaces of components comprising the medical instrument are physically and/or chemically modified to change their contact properties with respect to each other, bodily tissues, fluids or any other material with which they may come in contact. For example, coatings providing electrical conductivity, insulation, pharmacological activity, lubrication, hydroplasticity and/or hydrophobicity may be applied.

In accordance with one preferred embodiment of this invention, remote face 41 of partially hollow body 10 comprises means for maneuvering the medical instrument of this invention in the hollow structures such as arteries and veins, of its intended use. Such means include, but are not limited to, stiff or flexible tubes, reinforced tubes and spirals.

In summary, each embodiment of the instrument of this invention comprises the following essential elements:

Base bodies 26 and 27, to which at least two cutting bodies having cutting edges are connected, which cutting bodies open and close in scissorlike fashion by adjustment of an at least partially hollow body or of the clamping bodies. In the operating state, the cutting edges 24 are disposed substantially outside the at least partially hollow body and protrude past the base body 26, and upon actuation of the instrument, the cutting edges operatively contact the inner wall of the vessels.

I claim:

1. In a medical instrument for removing deposits on the walls of at least one of arteries and veins having at least one partially hollow body (10–14) that can be introduced into said at least one of said arteries and said veins, having at least one of a traction means and an actuation means (20) that are removable from said at least one of said arteries and said veins, and having a plurality of cutting bodies (21, 22), each of said cutting bodies (21,22) having at least one cutting edge (24) that points in a traction direction and removes the deposits, the improvement comprising:

a base body (26, 27) protruding at least one partially into the at least partially hollow body (10–14), and said plurality of cutting bodies (21, 22) extending in the traction direction fixedly connected to said base body (26, 27).

2. In a medical instrument in accordance with claim 1, wherein a portion (30) of the base body (26, 27) protruding into the at least one partially hollow body (10–14) is embodied as a tubular portion, in which a device (32, 34) for relative adjustment of the at least partially hollow body (10–14) with respect to said plurality of cutting bodies (21, 22) is disposed.

3. In a medical instrument in accordance with claim 2, wherein the device (32, 34) is embodied as a length of one of a tube and a wire that is actuatable from outside said at least one of said arteries and said veins.

4. In a medical instrument in accordance with claim 3, wherein said plurality of cutting bodies (21, 22) are formed of one of leaflet springs and a shape memory material.

5. In a medical instrument in accordance with claim 4, wherein the base body (26, 27) comprises a stop (38), which in the rest position of said plurality of cutting bodies (21, 22) is disposed virtually unspaced apart from an end face (40) of said at least one partially hollow body (10–14) facing said base body (26, 27).

6. In a medical instrument in accordance with claim 5, wherein the at least one partially hollow body (10–14) is embodied as a hollow cylinder which receives the cutting bodies (21, 22) in their rest position.

7. In a medical instrument in accordance with claim 6, wherein a remote face end (41) of the at least one partially hollow body (10–14) facing away from said base body (26, 27) has an opening (42) extending in the traction direction.

8. In a medical instrument in accordance with claim 7, wherein said remote face end (41) of the at least one partially hollow body (10–14) is convex and free of edges.

9. In a medical instrument in accordance with claim 8, wherein an external profile of a longitudinal section of each of said cutting bodies (21, 22) is curved.

10. In a medical instrument in accordance with claim 9, wherein at least one of the at least one partially hollow body (10–14) and the base body (26, 27) forms a transverse bore (60, 61) for guide means.

11. In a medical instrument in accordance with claim 10, wherein the plurality of cutting bodies (21, 22) define a hollow space (52) embodied as a chamber, through which the device (30, 32) extends.

12. In a medical instrument in accordance with claim 11, wherein each of said cutting bodies (21, 22) comprises at least one flank (54, 55) adjoining each of the cutting edges (24), each said flank (54, 55) comprising at least one cutting portion.

13. In a medical instrument in accordance with claim 12, wherein said plurality of cutting bodies (21, 22) extending in the traction direction are connected by at least one of screws, welding, hard soldering, and cold deformation, to said base body (26, 27) and their operating and rest positions are definable by adjustment of the at least one partially hollow body (10–14) in the traction direction.

14. In a medical instrument in accordance with claim 13, wherein the plurality of cutting bodies (21, 22) comprise an elastically deformable material selected from the group consisting of metal, ceramic, plastic, and alloys.

15. In a medical instrument in accordance with claim 14, wherein
the at least one partially hollow body (10–14), the base body (26, 27), and a portion of the plurality of cutting bodies (21, 22) comprise electrically conductive material and are coated with at least one of an insulator, a hydrophilic coating, and a pharmacologically active coating except for the cutting edges (24).

16. In a medical instrument in accordance with claim 15, wherein
at least two pairs of said plurality of cutting bodies (21, 22) are disposed in series.

17. In a medical instrument in accordance with claim 2, wherein
the plurality of cutting bodies (21, 22) define a hollow space (52) embodied as a chamber, through which the device (32,34) extends.

18. In a medical instrument in accordance with claim 1, wherein the base body (26, 27) comprises a stop (38), which in the rest position of said plurality of cutting bodies (21, 22) is disposed virtually unspaced apart from an end face (40) of said at least one partially hollow body (10–14) facing said base body (26, 27).

19. In a medical instrument in accordance with claim 1, wherein
the at least one partially hollow body (10–14) is embodied as a hollow cylinder which receives the cutting bodies (21, 22) in their rest position.

20. In a medical instrument in accordance with claim 1, wherein
a remote face end (41) of the at least one partially hollow body (10–14) facing away from said base body (26, 27) has an opening (42) extending in the traction direction.

21. In a medical instrument in accordance with claim 20, wherein
said remote face end (41) of the at least one partially hollow body (10–14) is convex and free of edges.

22. In a medical instrument in accordance with claim 1, wherein
an external profile of a longitudinal section of each of said cutting bodies (21, 22) is curved.

23. In a medical instrument in accordance with claim 1, wherein
at least one of the at least one partially hollow body (10–14) and the base body (26, 27) forms a transverse bore (60, 61) for guide means.

24. In a medical instrument in accordance with claim 1, wherein
each of said cutting bodies (21, 22) comprises at least one flank (54, 55) adjoining each of the cutting edges (24), each said flank (54, 55) comprising at least one cutting portion.

25. In a medical instrument in accordance with claim 1, wherein
each of the plurality of cutting bodies (21, 22) comprise one of at least one formed-on leaflet spring and one shape memory material.

26. In a medical instrument in accordance with claim 1, wherein
said plurality of cutting bodies (21, 22) extending in the traction direction are connected by at least one of screws, welding, hard soldering, and cold deformation, to said base body (26, 27) and their operating and rest positions are definable by adjustment of the at least partially hollow body (10–14) in the traction direction.

27. In a medical instrument in accordance with claim 1, wherein
the plurality of cutting bodies (21, 22) comprise an elastically deformable material selected from the group consisting of metal, ceramic, plastic, and alloys.

28. In a medical instrument in accordance with claim 1, wherein
the at least partially hollow body (10–14), the base body (26, 27), and
a portion of the plurality of cutting bodies (21, 22) comprise electrically conductive material and are coated with at least one of an insulator, a hydrophilic coating, and a pharmacologically active coating except for the cutting edges (24).

29. In a medical instrument in accordance with claim 1, wherein at least two pairs of said plurality of cutting bodies (21, 22) are disposed in series.

* * * * *